United States Patent [19]

Karol et al.

[11] Patent Number: 5,391,756
[45] Date of Patent: Feb. 21, 1995

[54] AROMATIC AMINE DERIVATIVES OF 2,5-DIMERCAPTO-1,3,4,-THIADIAZOLES

[75] Inventors: Thomas J. Karol, Norwalk; Steven G. Donnelly, New Fairfield, both of Conn.

[73] Assignee: R. T. Vanderbilt Company, Inc., Norwalk, Conn.

[21] Appl. No.: 979,682

[22] Filed: Nov. 20, 1992

[51] Int. Cl.$^6$ .................................. C07D 285/125
[52] U.S. Cl. .................................................. 598/112
[58] Field of Search ................................. 548/142

[56] References Cited

U.S. PATENT DOCUMENTS

| | | | |
|---|---|---|---|
| 2,765,289 | 10/1956 | Fields et al. | 252/32.7 |
| 4,740,454 | 4/1988 | Deguchi et al. | 430/567 |
| 4,925,580 | 5/1990 | Camenzind | 252/47 |
| 4,990,273 | 2/1991 | Croudace | 252/46.4 |
| 5,147,569 | 9/1992 | DeRosa et al. | 252/47.5 |

FOREIGN PATENT DOCUMENTS 275449  7/1988  European Pat. Off. ............ 548/142

*Primary Examiner*—Robert Gerstl
*Attorney, Agent, or Firm*—Rasma B. Balodis

[57] ABSTRACT

Disclosed are novel compounds prepared by reacting 2,5-dimercapto-1,3,4-thiadiazole, aliphatic or aromatic aldehyde and aromatic amine in the molar ratio of 1:1:1 to 2:4:3. The 2,5-dimercapto-1,3,4-thiadiazole may be substituted in the 2-position by hydrocarbyl, terpene, polymeric and succinate residues. The compounds possess antiwear and antioxidant characteristics.

3 Claims, 1 Drawing Sheet

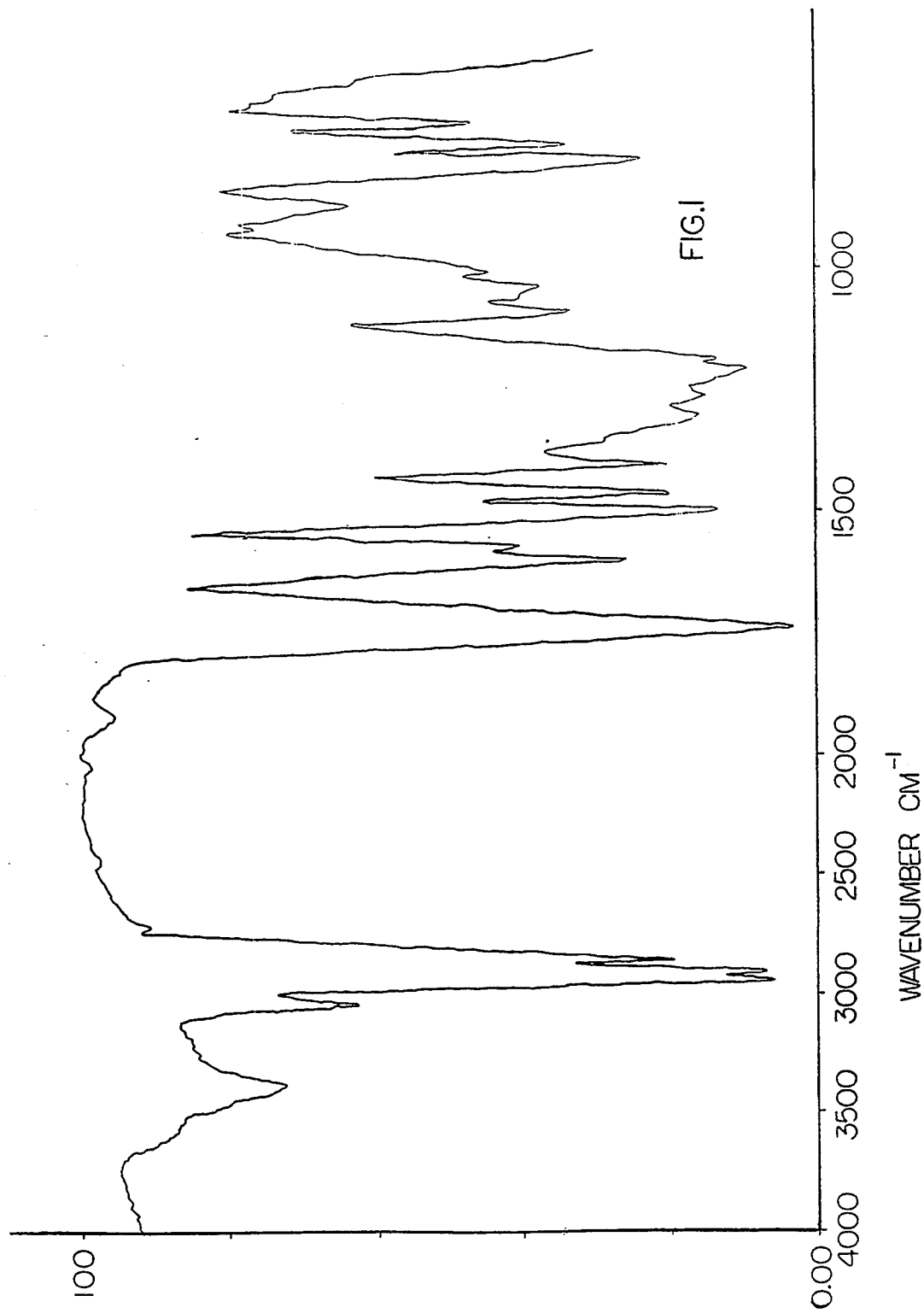

AROMATIC AMINE DERIVATIVES OF 2,5-DIMERCAPTO-1,3,4,-THIADIAZOLES

BACKGROUND OF THE INVENTION

The present invention concerns aromatic amine derivatives of thiadiazole compounds. More particularly, the thiadiazoles are derived from 2,5-dimercapto-1,3,4-thiadiazole, an aldehyde and an aromatic amine compound.

U.S. Pat. No. 2,765,289 teaches reaction products of 2,5-dimercapto-1,3,4-thiadiazoles, aldehyde and diarylamine having an aldehyde-carbon to nitrogen bond. The products possess corrosion inhibiting properties.

U.S. Pat. No. 4,990,273 discloses similar reaction products having extreme pressure and antiwear properties.

U.S. Pat. No. 5,147,569 discloses reaction products of glycidyl methacrylate grafted polyolefinic epoxide and 1,3,4-thiadiazole containing a substituted diarylamine or a substituted phenothiazine. The compounds function as viscosity index improvers, antioxidants and antiwear agents.

An object of the invention is to provide novel reaction products of 2,5-dimercapto-1,3,4-thiadiazole, aldehyde and certain aromatic amines having the aldehyde-carbon bonded to the aromatic ring instead to the nitrogens. Another object is to provide products having antiwear and antioxidant properties when incorporated into lubricating compositions.

SUMMARY OF THE INVENTION

In accordance with the invention, there are provided novel 1,3,4-thiadiazole compounds characterized by the structural formulae

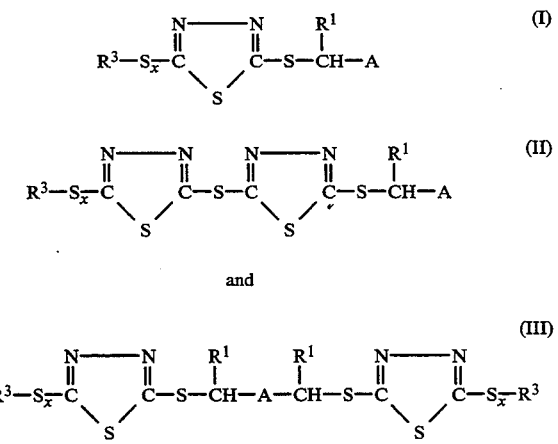

wherein x=1–2, R represents the group

alkyl, cycloalkyl, aralkyl, terpene residue, and a succinate residue of the formula

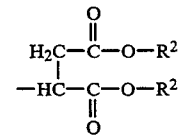

$R^1$ represents hydrogen, $C_{1-17}$-alkyl, phenyl and phenyl substituted by alkyl groups; A represents aromatic ring structure selected from the group consisting of N'-phenyl-p-phenylenediamine, diphenylamine, naphthylamine, quinoline, hydrated quinoline, phenothiazine, and phenyl-(1 or 2)-naphthylamine and wherein the aromatic ring and amine groups may be substituted by alkyl groups; $R^2$ represents hydrogen, alkyl and cycloalkyl groups; and $R^3$ represents the group R and a polymeric alpha-olefin residue which contains 20 to 100 carbon atoms and is unsubstituted or has a substituent hydroxy group in the 2 position.

FIG. 1 shows the infrared spectrum of the present reaction product of 2-(1,2-di(2-ethylhexoxycarbonyl)ethylthio)-1,3,4-thiadiazole, paraformaldehyde and phenyl-1-naphthylamine and further described in Example 2 hereinbelow.

The absorption in the region of 3324 to 3392 cm$^{-1}$ indicates N—H bond absorption.

DESCRIPTION OF SPECIFIC EMBODIMENTS

The novel compounds of the invention may be prepared by reacting 2,5-dimercapto-1,3,4-thiadiazole, aldehyde and an aromatic amine by an alkylation process. Preferred are reaction products wherein the thiadiazole, aldehyde and aromatic amine ranges in the molar ratio of 1:1:1 to 2:4:3.

The reaction is essentially an alkylation process wherein the 2,5-dimercapto-1,3,4-thiadiazole and aldehyde form a hydroxy-intermediate which attaches to a carbon atom on the aromatic ring of the amine. The position of attachment to the ring may vary and mixtures may be formed. The products are characterized by aromatic amine N-H bond stretching absorption in the region of 3175 to 3450 cm$^{-1}$.

The reaction may be conducted in the presence or absence of a suitable inert solvent, such as toluene, dimethyl ether and others. Optionally, the reaction may employ acid catalysts. For example, a Lewis acid catalyst such as methanesulfonic acid may be used.

An alternate alkylation process may be employed wherein a Lewis acid is used as a blocking agent for the aromatic amine group. A particularly preferred Lewis acid is acetyl chloride. The blocked amine is reacted with 2,5-dimercapto-1,3,4-thiadiazole compound and aldehyde to form an intermediate product. The intermediate is hydrolyzed with a strong base and the product is isolated. In some cases, a weak Lewis acid, e.g. AlCl$_3$ can be eliminated by addition of water. The reaction is conducted in the presence of solvents such as dioxane, hexane, and similar inert organic solvents. In the case of bicyclic aromatic amines, the alkylation process using the blocking agent produces higher yields of the alkylated product.

The aldehyde reactant may be a normal or branched chain aliphatic aldehyde containing 1 to 18 carbon atoms or an aromatic aldehyde. Examples of suitable aldehydes include, among others, formaldehyde, acetaldehyde, benzaldehyde, 2-ethylhexyl aldehyde, butyraldehyde, caprylic aldehyde, phenylacetaldehyde, and salicylaldehyde.

The aromatic amine may be selected from aromatic monoamines and diamines. The aromatic compounds may be substituted by alkyl groups on the amine group and the aromatic ring. The alkyl groups may be normal or branched chain. Particularly preferred are alkyl groups having 1 to 18 carbon atoms. Specific compounds include, among others, diphenylamine, alkylated diphenylamine such as 4,4'-dioctylphenylenediamine, phenylenediamine, alkylated phenylenediamine, N,N'-dioctylphenylenediamine, N-(1,3-dimethylbutyl)-N'-phenyl-p-phenylenediamine, phenothiazine, phenyl-1-naphthylamine, phenyl-2-naphthylamine, 1,2-dihydro-2,2,4-trimethylquinoline and its polymers.

The novel 1,3,4-thiadiazole derivatives may be substituted in the 5-position by alkyl, cycloalkyl, aryl and aralkyl groups, terpene residues, polymeric alpha-olefin residues and succinate residues. The alkyl groups may be straight or branched chain and may contain up to 100 carbon atoms. Representative alkyl groups, among others, include methyl, butyl, 2-ethylhexyl, dodecyl, and octadecyl groups. Exemplary cycloalkyl groups include cyclopentyl, cyclohexyl and cycloheptyl. Preferred aryl groups are phenyl, naphthyl, phenothiazinyl and quinolyl groups. Particularly preferred terpene residues are pinene residue of the formula

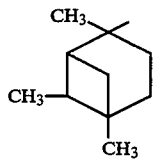

and limonene residue of the formula

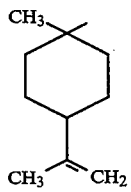

The polymeric alpha-olefin residue is essentially a hydrocarbyl radical having 20 to 200 carbon atoms. Typically, the molecular weight of the polymeric residue ranges from 280 to 2600 and higher. Preferred are polymers having olefinic unsaturation. The polymers may have straight or branched chain aliphatic units having 2 to 10 carbon atoms. Especially useful are polymers and copolymers of alpha-olefins as for example isoprene, isobutene, 2-methyl-1-heptene, ethylene, propylene, and 2-methyl-5-propylhexene. The polymeric residue may be derived from a hydrocarbon polymer with an epoxide or chlorine functionality. Activated polyolefins are available commercially. Activated polyisobutenes with epoxide functionality are marketed under the trade name ACTIPOL TM by Amoco Chemical Company. Alternately, commercial polyolefins may be epoxidized by known methods.

The succinate residue in the above formulae may be derived from maleic anhydride or acid and further esterified with normal and branched chain alkyl groups containing 1 to 22 carbon atoms and cyclic aliphatic groups such as cyclohexyl, cyclopentyl and cycloheptyl.

The thiadiazole derivatives of the invention are useful as additives for lubricants. The compounds possess multifunctional properties. In addition to being effective antiwear agents, they also perform oxidation inhibiting functions.

The amount of the thiadiazole additive required to be effective for imparting antiwear and antioxidant characteristics to lubricating compositions may range from about 0.01 to 15.0 percent of the lubricating composition. The preferred range is about 0.1 to 5.0 percent of the additive based on the weight of the lubricating composition.

The base oil of the lubricants may be selected from naphthenic, aromatic, paraffinic, mineral and synthetic oils. The synthetic oils may be selected from, among others, alkylene polymers, polysiloxanes, carboxylic acid esters and polyglycol ethers.

The lubricating compositions may contain the necessary ingredients to formulate the composition, as for example emulsifiers, dispersants and viscosity improvers. Greases may be prepared by adding thickeners, as for example, salts and complexes of fatty acids, polyurea compounds, clays and quaternary ammonium bentonite complexes. Depending on the intended use of the lubricant, other functional additives may be added to enhance a particular property of the lubricant. The lubricating compositions may further contain extreme pressure agents, metal passivators, rust inhibitors, dispersants and other known antioxidants and antiwear agents.

The following examples are given for the purpose of further illustrating the invention. All percentages and parts are based on weight unless otherwise indicated.

EXAMPLE 1

2-Pinanyl-5-(4,4'-dioctylphenylamino-(o or m)-phenylene)methylenethio-1,3,4-thiadiazole A reactor was charged with alpha-pinene, 49.0 g (0.36 moles), 2,5-dimercapto-1,3,4-thiadiazole, 53.3 g (0.36 moles) and toluene, 50 ml. The reaction mixture was cautiously heated to 130°-140° C., followed by addition of 91% paraformaldehyde, 12.2 g (0.37 moles). After heating for one hour, the reactor was charged with p,p'-dioctyldiphenylamine, 141.5 g (0.36 moles) and toluene, 50 ml. Water was azeotroped off at about 135° C. The product was stripped and filtered.

EXAMPLE 2

Reaction product of 2-(1,2-di(2-ethylhexoxycarbonyl)ethylthio)-1,3,4-thiadiazole, paraformaldehyde and phenyl-1-naphthylamine.

A reactor was charged with 2-(1,2-di(2-ethylhexoxycarbonyl)ethylthio)-1,3,4-thiadiazole, 1400 g and 91% paraformaldehyde, 110 g and heated at about 130°-135° C. for about 0.5 hours. The intermediate, 160.4 g and phenyl-1-naphthylamine, 69.2 g and toluene, 100 ml was added and water was azeotroped off at about 135° C. The product was stripped and filtered. Infrared spectrum presented in FIG. 1 showed good N—H bond absorption in the region of 3324 to 3392 cm$^{-1}$.

EXAMPLE 3

Reaction product of 2-pinanyl-1,3,4-thiadiazole-5-thiol, isobutyraldehyde and diphenylamine A reactor was charged with alpha-pinene, 75 g, 2,5-dimercapto-1,3,4-thiadiazole, 75 g and rinsed with acetone, 3 ml. The reaction was heated cautiously to 130°–135° C. for 5 minutes. The reaction was stripped of excess pinene and acetone with aspirator under reduced pressure. After cooling to 50° C., the reaction was charged with isobutyraldehyde, 40 g and diphenylamine, 83.5 g. The reactor was fitted with Dean Stark attachment filled with hexane and heated to 130° C. After collecting water, the hexane volume was adjusted for a reflux at 130° C. and the reaction was azeotroped for 8 hours. The product was stripped and filtered.

EXAMPLE 4

Reaction product of 2-hydroxymethylthio-1,3,4-thiadiazole-5-thiol and diphenylamine A reactor was charged with 2,5-dimercapto-1,3,4-thiadiazole, 30 g, and 100 ml dioxane and mixed. After addition of 37% formaldehyde, 16.3 g, water was azeotroped with hexane. Diphenylamine, 33.85 g, was added and the mixture was heated to azeotrope water. After cooling to room temperature, the mixture was dried over magnesium sulfate, filtered and the solvent was stripped off under vacuum at 110° to 115° C.

EXAMPLE 5

Reaction product of p,p'-dinonyldiphenylamine, formaldehyde, and 2-mercapto-1,3,4-thiadiazole monosulfide dimer was prepared by the blocking method A reactor fitted with a reflux condenser was charged with p,p'-dinonyldiphenylamine, 100.3 g, and acetyl chloride, 30.0 g. The reaction was heated to reflux for 0.5 hour and then stripped of HCl and excess acetyl chloride by applying vacuum. After cooling, the reaction was charged with 2-mercapto-1,3,4-thiadiazole monosulfide dimer, 32.5 g, dioxane, 150 ml, 37 percent formaldehyde, 20.0 g, and hexane, 25 ml. The reaction was fitted with a Dean Stark trap filled with 25 ml hexane. The reaction was brought to reflux and water was azeotroped until none was evolved.

The intermediate product was stripped of solvents by applying vacuum. The intermediate was filtered by diluting with ether and tetrahydrofuran. The intermediate was then hydrolyzed by charging 25 g of 50 percent sodium hydroxide solution and refluxing for 2 hours. The hydrolyzed product was isolated by extraction into ether from water. The ether layer was dried over magnesium sulfate, filtered, and stripped to afford the product.

For comparison, the same procedure was conducted without the blocking step. Both methods of alkylation demonstrated infrared absorption in the region of the N-H bond stretching. The reaction conducted without the blocking step yielded lower ring alkylation. In the case of the blocked material, the ring alkylation was estimated to be complete.

EXAMPLE 6

Thin Film Oxygen Uptake Test

A test was conducted essentially according to the method described by Chia-Soon Ku et al, *J. Am. Soc. Lubricating Eng.*, 40, 2,75–83, 1984. The oxidation induction time of the lubricant was measured under conditions which simulate the high temperature oxidation process in automotive engines by a modified rotary bomb oxidation test method ASTM D-2272. The test was conducted with 1.5 gram samples of SAE 30, motor oil. The oil was fully formulated with the exception of the antioxidant additive. The test was conducted at 160° C. and initial oxygen pressure of 620.6 kPa (90 psi). A "pass" oil has a high induction time, while a "fail" oil has a low induction time. Compounds of the invention were added to the oil in the amount indicated in Table I. The data indicate that the additives of the invention have good antioxidant properties.

EXAMPLE 7

Modified Falex Wear Test

A laboratory test was conducted by using the original Falex machine to simulate the valve train wear of an automobile engine. The V-blocks and pin were washed in mineral spirits with an ultrasonic cleaner, rinsed with acetone, air-dried and weighed. The test sample (60 g) was placed into the oil cup. The motor was switched on and the loading arm was placed on the ratchet wheel. Upon reaching the reference load of 227 kg, the ratchet wheel was disengaged and the load was maintained constant for 3.5 hours. Thereafter, the motor was switched off. The V-blocks and pin were washed, dried and weighed. The weight loss, a measure of wear, was recorded and compiled in Table II.

The test samples were prepared by adding the compounds of the invention to the base motor oil (SAE 30, SF) in the amount given in Table II. The base oil contained 0.11 percent phosphorus and no supplemental antioxidant. The results indicate that the present compounds afford good antiwear properties.

TABLE I

Thin Film Oxygen Uptake Test

| Sample | Antioxidant Additive | Percent | Average Induction Time, min. |
|---|---|---|---|
| 1 | — | — | 108 |
| 2 | Compound of Example 3 | 0.35 | 154 |
| 3 | 2-(1,2-di(2-ethylhexoxycarbonyl)-ethylthio)-5-(4,4'-dioctylphenylamino-(o or m)-phenylene)-methylenethio-1,3,4-thiadiazole | 0.35 | 138 |
| 4 | 2-(1,2-di(2-ethylhexoxycarbonyl)-ethylthio)-5-(4-phenylamino-p-phenylene)-methylenethio-1,3,4-thiadiazole | 0.35 | 138 |

TABLE II

Falex Wear Test

| Sample | Antiwear Additive | Percent | Total Weight Loss, mg |
|---|---|---|---|
| 5 | — | — | 57.2 |
| 6 | 2-(1,2-di(2-ethylhexoxycarbonyl)ethylthio)-5-(4,4'-dioctylphenylamino-(o or m)-phenylene)-methylenethio-1,3,4-thiadiazole | 0.35 | 3.4 |
| 7 | 2-(1,2-di(2-ethylhexoxycarbonyl)-ethylthio)-5-(4-phenylamino-p-phenylene)-methylenethio-1,3,4- | 0.35 | 22.0 |

TABLE II-continued

Falex Wear Test

| Sample | Antiwear Additive | Percent | Total Weight Loss, mg |
|---|---|---|---|
| | thiadiazole | | |

The above embodiments have shown various aspects of the present invention. Other variations will be evident to those skilled in the art and such modifications are intended to be within the scope of the invention as defined by the appended claims.

What is claimed is:

1. A thiadiazole compound selected from the group of compounds having the structural formula

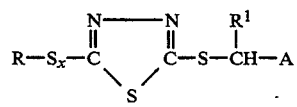

wherein x=1–2, R represents the group

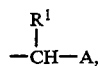

alkyl having up to 100 carbon atoms, cycloalkyl, aralkyl, terpene residue selected from pinene and limonene, and a succinate residue of the formula

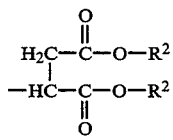

$R^1$ represents hydrogen, $C_{1-17}$-alkyl, phenyl and phenyl substituted by alkyl groups; A represents aromatic ring structure selected from the group consisting of N'-phenyl-p-phenylenediamine, diphenylamine, naphthylamine, quinoline, hydrated quinoline, phenothiazine, and phenyl-(1 or 2)-naphthylamine and wherein the aromatic ring and amine groups may be substituted by $C_{1-18}$-alkyl groups provided that A is bonded at a carbon atom of the ring; and $R^2$ represents hydrogen, $C_{1-22}$-alkyl and cycloalkyl groups.

2. A thiadiazole compound selected from the group of compounds having the structural formula

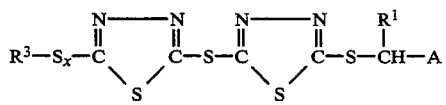

wherein x=1–2, $R^3$ represents the group

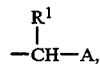

alkyl having up to 100 carbon atoms, cycloalkyl, aralkyl terpene residue selected from pinene and limonene, a polymeric alpha-olefin residue which contains 20–100 carbon atoms and is unsubstituted or has a substituent hydroxy group in the 2-position, and a succinate residue of the formula

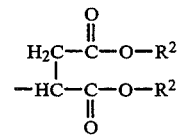

$R^1$ represents hydrogen, $C_{1-17}$-alkyl, phenyl and phenyl substituted by alkyl groups; A represents aromatic ring structure selected from the group consisting of N'-phenyl-p-phenylenediamine, diphenylamine, naphthylamine, quinoline, hydrated quinoline, phenothiazine, and phenyl-(1 or 2)-naphthylamine and wherein the aromatic ring and amine groups may be substituted by $C_{1-18}$-alkyl groups provided that A is bonded at a carbon atom of the ring; and $R^2$ represents hydrogen, $C_{1-22}$-alkyl and cycloalkyl groups.

3. A thiadiazole compound selected from the group of compounds having the structural formula

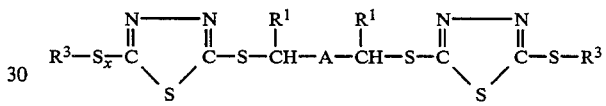

wherein x=1–2, $R^3$ represents the group

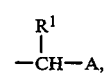

alkyl having up to 100 carbon atoms, cycloalkyl, aralkyl, terpene residue selected from pinene and limonene, a polymeric alpha-olefin residue which contains 20–100 carbon atoms and is unsubstituted or has a substituent hydroxy group in the 2-position, and a succinate residue of the formula

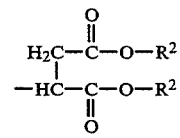

$R^1$ represents hydrogen, $C_{1-17}$-alkyl, phenyl and phenyl substituted by alkyl groups; A represents aromatic ring structure selected from the group consisting of N'-phenyl-p-phenylenediamine, diphenylamine, naphthylamine, quinoline, hydrated quinoline, phenothiazine, and phenyl-(1 or 2)-naphthylamine and wherein the aromatic ring and amine groups may be substituted by $C_{1-18}$-alkyl groups provided that A is bonded at a carbon atom of the ring; and $R^2$ represents hydrogen, $C_{1-22}$-alkyl and cycloalkyl groups.

* * * * *

UNITED STATES PATENT AND TRADEMARK OFFICE
CERTIFICATE OF CORRECTION

PATENT NO. : 5,391,756
DATED : February 21, 1995
INVENTOR(S) : Thomas J. Karol et al It is certified that error appears in the above-indentified patent and that said Letters Patent is hereby corrected as shown below:

On the title page, item [54] and column 1 lines 1-3 the title;

"2,5-DIMERCAPTO-1,3,4-THIADIAZOLES" should read

--2,5-DIMERCAPTO-1,3,4-THIADIAZOLES--;

Column 1, line 45, formula I

"$R^3-S_x-$" should read --$R-S_x-$ --;

Column 6, line 6

"SAE 30, motor oil" should read

--SAE 30, SF motor oil--;

Column 6, line 49, Table I

Insert --0.35-- under Percent column and

Insert --139-- under Time, min. column.

Signed and Sealed this

Eleventh Day of April, 1995

Attest:

BRUCE LEHMAN

Attesting Officer     Commissioner of Patents and Trademarks